United States Patent [19]

Lansbarkis et al.

[11] Patent Number: 5,719,322
[45] Date of Patent: Feb. 17, 1998

[54] ZEOLITIC CAPILLARY COLUMNS FOR GAS CHROMATOGRAPHY

[75] Inventors: James R. Lansbarkis, El Dorado, Calif.; Stephen T. Wilson, Libertyville; Hermann A. Zinnen, Evanston, both of Ill.

[73] Assignee: UOP, Des Plaines, Ill.

[21] Appl. No.: 730,719

[22] Filed: Sep. 20, 1996

[51] Int. Cl.$^6$ .......................... B01D 15/08; G01N 30/08; B01N 61/42

[52] U.S. Cl. .................. 73/23.39; 73/23.35; 73/61.53; 422/88; 210/198.2

[58] Field of Search ................... 73/23.39, 23.35, 73/61.53, 61.52; 422/89, 88; 55/67; 428/91; 210/198.2, 198.3

[56] References Cited

U.S. PATENT DOCUMENTS

| | | | |
|---|---|---|---|
| 3,169,390 | 2/1965 | Roper, Jr. | 73/23.1 |
| 3,392,507 | 7/1968 | Ottenstein | 55/67 |
| 3,443,416 | 5/1969 | Webb | 73/23.1 |
| 3,471,261 | 10/1969 | Patterson | 23/230 |
| 3,530,707 | 9/1970 | Zimmermann | 73/23.1 |
| 3,547,684 | 12/1970 | Hollis et al. | 117/95 |
| 3,650,090 | 3/1972 | Temple et al. | 55/31 |
| 3,651,618 | 3/1972 | Klein et al. | 55/16 |
| 3,796,657 | 3/1974 | Pretorius et al. | 210/31 C |
| 3,808,125 | 4/1974 | Good | 210/31 C |
| 4,123,931 | 11/1978 | Blaser | 73/23.1 |
| 4,169,790 | 10/1979 | Pretorius et al. | 210/31 C |
| 4,293,415 | 10/1981 | Bente, III et al. | 210/198.2 |
| 4,479,380 | 10/1984 | Novotny et al. | 73/61.1 C |
| 4,534,207 | 8/1985 | Szakasits et al. | 73/23.1 |
| 4,805,441 | 2/1989 | Sides et al. | 73/23.1 |
| 4,931,328 | 6/1990 | Swedberg | 428/36.91 |
| 5,027,643 | 7/1991 | Jenkins | 73/23.39 |
| 5,262,031 | 11/1993 | Lux et al. | 204/299 |
| 5,498,478 | 3/1996 | Hansen et al. | 428/372 |
| 5,543,456 | 8/1996 | Iriguchi et al. | 524/542 |
| 5,552,042 | 9/1996 | LeFebre et al. | 210/198.2 |

*Primary Examiner*—Hezron E. Williams
*Assistant Examiner*—J. David Wiggins
*Attorney, Agent, or Firm*—Thomas K. McBride; Eugene I. Snyder

[57] ABSTRACT

Methods have been found to prepare fused silica capillary gas chromatographic columns where the stationary phase is a molecular sieve affixed to the silica capillary wall without the aid of an organic binder by modifying the interior surface of the silica prior to contact with the molecular sieve. These totally inorganic columns greatly expand the application and range of gas chromatographic separations and allow the use of non-traditional carrier gases, even air, while not degrading the separation of components. The columns are films of small molecular sieve particles affixed to a silica surface modified by such treatments as hydrogen peroxide, alumina deposition, or silica deposition followed by fixation at 80°–160° C.

12 Claims, No Drawings

ZEOLITIC CAPILLARY COLUMNS FOR GAS CHROMATOGRAPHY

BACKGROUND OF THE INVENTION

A gas chromatograph is built around the central theme of a gas chromatographic column containing a packing which effects separation of materials present in a gas stream. The packing typically was in the form of a solid plug of small particles, coated or not, which filled most of the interior of a tubular column. At the outset of this technique columns were fabricated from copper, aluminum, stainless steel, and glass, and generally had an inside diameter of several millimeters. Even in the early days gas solid chromatography was an important variant, that is, materials were partitioned between the gas and a solid phase of a packed column. Since zeolites—or more generally molecular sieves—were recognized as having the outstanding capability of effecting separation among materials based on size discrimination, they were routinely used per se as a packing for separation of gases such as hydrogen, oxygen, nitrogen, carbon monoxide, methane, and so on. As increasingly diverse molecular sieves became available their utility in the separation of organic materials, especially lower molecular weight compounds, was recognized and applied.

The year 1979 brought a marked change to gas chromatography arising from the introduction of inert fused silica capillary columns; see U.S. Pat. No. 4,293,415. The use of packed large bore columns declined and capillary column replacements typically constituted a stationary phase as a thin coating on the capillary walls, surrounding an open passageway for gas flow, rather than the solid plug previously found in large bore columns. This drastic change in column geometry and stationary phase distribution resulted in the vastly superior performance of capillary columns relative to packed large bore columns which is legion and which some believe has become synonymous with the term "high-resolution gas chromatography." See "Modern Practice of Gas Chromatography," R. L. Grob, Ed., J. Wiley & Sons (1995), page 154.

The profoundly different nature of capillary columns requires profoundly different methods of depositing the stationary phase, which in the vast majority of cases is an organic material. The goal in introducing a stationary phase into capillary columns is to uniformly deposit a film on the order of 0.1–10 microns thick on the inner wall. One frequently employed method is solution coating, where the column is filled with the solution of the organic stationary phase and the solvent, usually pentane, is evaporated at a reduced pressure. However simple this may sound, practical complexities arise from the need for passivation (deactivation) of the fused silica surface itself; thin film fragility, and long term thermal and chemical instability of the film, inter alia. Thus early capillary columns suffered from limitations associated with the film itself.

Subsequent advances in stationary phase coating led to a significant stabilization of films via immobilization of the organic stationary phase. One general technique is in situ crosslinking of the organic stationary phase effected by a rich diversity of free radical initiators, including gamma radiation. More recently film stabilization has been achieved via chemical bonding of the organic stationary phase to fused silica, generally by reaction of appropriate functional groups on the stationary phase with surface silanol (Si-OH) groups of fused silica. In principle, as well as in practice, chemical bonding achieves both deactivation of the fused silica surface and film stabilization concurrently. For a review see R. L. Grob, op. cit.

Contemplation of the use of inorganic molecular sieves as the stationary phase in capillary columns immediately raises problems whose solutions are not readily apparent. Since molecular sieves are insoluble in solvents generally used in solution coating, a thin film of a molecular sieve cannot be deposited by this common technique. Film fragility is perhaps an even greater problem, since one can expect a thin film of a molecular sieve to be quite brittle and easily subject to cracking, especially upon thermal cycling. Film stability via crosslinking and/or chemical bonding to fused silica requires solutions much different from those used for traditional organic stationary phases in capillary columns. Yet the incentive for arriving at solutions to these problems is substantial, since separations based on molecular sieve properties can be expected to be quite different from separations based on the organic stationary phases currently used for fused silica capillary columns. Thus, new vistas may open once methods are available for depositing stable thin films of inorganic solids on walls of fused silica capillaries. This application relates to such methods, the resulting gas chromatographic column, and gas chromatographic separations generally using the columns of our invention.

The chromatography prior art appears to be devoid of any viable analogs to our invention. What the prior art has invoked, at most, is a method of depositing a film of inorganic material on an organic binder interposed between the fused silica surface and the inorganic material. As an example, an organic polymer such as a carbowax-type material (i.e., polyethylene glycol) in which is dispersed inorganic material may be deposited on the fused silica as described above, and after removal of the solvent used as a carrier there remains a stable film of the inorganic material embedded in the film of organic polymer. The resulting column suffers from at least two distinct disadvantages: separations are affected by the organic binder, so that separations may be a complex function of the inorganic and binder phases; thermal stability is determined by the organic phase, with bleeding and decomposition of the binder occurring at temperatures well below the maximum at which the inorganic phase could serve.

The instant invention provides some general methods of bonding molecular sieve particles to the interior wall of a fused silica capillary to form a gas chromatographic column having a molecular sieve coating as a stationary phase devoid of any organic material. In a preferred embodiment, the bonding process is applied to particles whose size is less than 2 microns in order to more fully utilize the excellent discrimination and capacity of molecular sieves in gas-solid chromatographic separations. Our methods provide the adhesion between fused silica and molecular sieves necessary to afford films which are stable to thermal cycling and mechanical shock.

Our invention admits of the general use of molecular sieves as a stationary phase in fused silica capillary columns and thus eliminates some inherent weaknesses of conventional stationary phases. The ability to use air as the carrier gas would lower operating costs, allow the development of truly portable gas chromatographs, and allow the column to be "burned out" at high temp to remove any contamination. Since molecular sieves can be readily modified by a myriad of standard techniques (e.g., ion exchange, secondary synthesis), many derivations could be made to enhance separations of interest. Columns of our invention also dramatically decrease the amount of "detector bleed," caused by the stationary phase decomposition products passing through the detector, since molecular sieves are much more thermally stable than organic materials and would not cause most of the commonly used detectors to respond to their decomposition products. Elimination of the organic binder, typical of prior art columns containing inorganic materials as the stationary phase, also eliminates separation effects arising from the organic material itself.

SUMMARY OF THE INVENTION

The purpose of our invention is the preparation of fused silica capillary gas chromatographic columns having a stable thin film of a molecular sieve, and their application to the separation of diverse materials. In one embodiment the fused silica surface is treated with a 3-35 weight percent hydrogen peroxide solution, a coating of molecular sieve is deposited from a slurry, and the sieve is fixed by being heated at a temperature 80° C. or above. In a second embodiment a strongly adherent film of alumina is deposited on the fused silica by treatment aluminum chlorhydrate, followed by deposition of a molecular sieve. In yet another embodiment a strongly adherent film of silica is deposited on the fused silica by treatment with a silica precursor such as tetraethyl orthosilicate, followed by hydrolysis, and a sieve is deposited on the resulting film. Other variants will become apparent in the ensuing description.

DESCRIPTION OF THE INVENTION

Our invention is multifaceted, but each facet reflects a different aspect of gas chromatography. One aspect is that of a fused silica capillary gas chromatographic column having as the stationary phase a thin film of a molecular sieve on the interior surface and bounding the passageway for gas flow along the axis of the capillary. But the very existence of such a gas chromatographic column requires that the film be resistant to attrition by a flowing gas stream, and manifest excellent adhesion to the used silica with continued temperature cycling, gas flow rates, different analytes, and so on. These requisite properties are made possible only by applicants' methods of effecting durable adhesion of molecular sieve particles to fused silica, which constitute another aspect encompassed by our invention. With the novel columns of our invention many separations are facilitated, which form yet another aspect of our invention. It is clear that the various aspects cited above are but variations on the first-stated central theme—a new type of gas chromatographic column—but the variations are integrated with profound consequences, as will be apparent from the ensuing description. The preparation of the foregoing columns constitutes yet another theme—a theme which makes the foregoing ones possible.

Fused silica capillaries are well known to those in the field of gas chromatography; vide supra. Consequently little elaboration is deemed necessary. More recently a much improved fused silica capillary designed especially for gas chromatographic use with a solid stationary phase at high temperatures has been described by LeFebre, Gingrich, and Lansbarkis (American Laboratory, August, 1995, pp 13-14). In brief, the column is a fused silica capillary wrapped around, and sinter-fused to, a fused silica mandrel which provides rigidity and support and which obviates the need for a coating on the capillary outer wall since the tubing is stress-relieved by the annealing process by which it is sinter-fused to the mandrel. Such a column presents many advantages, and although the invention herein is clearly applicable to all fused silica capillaries, regardless of design, the rigid capillary column referred to above is preferred in the practice of our invention.

Molecular sieves as a class are well known adsorbents for a variety of species from elemental gases through complex organic materials and have been utilized under a variety of conditions. For example, they have been used as packed beds to effect gas-solid separations as well as liquid-solid separations, and processes utilizing their discriminatory separation ability range in scale from micrograms (e.g., analytical chromatography) to kilograms (e.g., commercial processes for separating isomeric aromatics). Although it is unnecessary to go into a long litany of materials which may be used as adsorbents in practicing this invention, one may mention as some of the more available and efficacious adsorbents silicalite, zeolites A, X, and Y, especially in a cation-exchanged form, dealuminated zeolites Y and L, ZSM-5, ZSM-12, zeolite omega, boralite, the classes designated as ALPOs, SAPOs and MeAPSOs, VPI-5, and so forth. However, it is to be clearly understood that molecular sieves as a class are within the scope of our invention. The adsorbent qualities of molecular sieves are not the subject of this invention, but are merely used by our invention. Consequently, our subsequent use of "molecular sieve" is intended to encompass the entire class of sieves generally, rather than any specific group.

The molecular sieve, or combination of molecular sieves, to be used as the stationary phase is deposited as a thin film, either directly on the inner surface of the fused silica capillary or on a thin coating of alumina or silica which itself adheres strongly to the fused silica surface. It is somewhat misleading to merely say the film is "deposited" on the fused silica surface, because more is necessary to achieve a film with good adhesion to the silica than just physically depositing it on the silica, and in fact the silica surface must be pretreated to enable good adhesion with the molecular sieve. The different pretreatments are characterized by the absence of organic binders, which serves to sharply differentiate the resulting coated columns from the prior art. Our pretreatments are not merely ancillary to our invention, but instead constitute key enablers of our invention and are solutions to the problem of forming thin films of molecular sieves with the stability requisite for deployment in gas chromatography.

We have observed that several types of disparate pretreatments are successful, although we describe below three pretreatments which are especially efficacious. In brief, the successful procedures include treating the silica surface with hydrogen peroxide, with acid, with base, with steam, especially superheated steam, with aluminum chlorohydrate, and with a refractory inorganic oxide precursor, but especially a silica precursor. Although the treatments are diverse we hypothesize that a common unifying element is that all of the foregoing methods effect hydroxylation of the fused silica surface, resulting in Si-OH groups associated with the fused silica. These groups can subsequently condense with Si-OH and/or Al-OH of a molecular sieve in contact with the fused silica surface to form Si-O-Si or Si-O-Al bonds. Alteratively, the Si-OH groups can condense with the Me-OH groups characteristic of other metal oxides deposited intermediate to the fused silica surface and molecular sieve coating. Although we can not vouch for this hypothesis, nor give experimental support therefor, it provides a conceptual framework and unifying theme which we found quite useful in our developmental efforts.

One method of pretreatment, or surface modification, involves contacting the silica with hydrogen peroxide either prior to or concurrent with contact with the molecular sieve, followed by heat fixation. In this pretreatment the fused silica surface is first contacted with a solution of a peroxide or hydroperoxide, with hydrogen peroxide being the most conveniently employed agent in this pretreatment method.

Concentrations of aqueous hydrogen peroxide from about 3 weight percent to about 35 weight percent have been found to be efficacious. Contact temperatures generally are in the range from about 60° up to about 90° C. with contact times from about 20 up to about 30 minutes using 35 weight percent hydrogen peroxide at 85° C. sufficient to ensure success. Clearly, contact time will vary with temperature and hydrogen peroxide concentration, but appropriate times may be readily determined by simple experimentation.

As stated above, the molecular sieves of our invention are characterized by surface Si-OH or Al-OH groups. Although firm experimental supporting evidence is unavailable, it is believed that good adhesion between the molecular sieve particles and the surface modified fused silica arises by condensation between the silica Si-OH and the sieve Si-OH (or Al-OH) groups to form stable Si-O-Si (or Si-O-Al) linkages. Such condensation does not occur spontaneously, but rather is facilitated by treatment at temperatures of about 80° C. or more, generally between about 80° and about 160° C. Consequently, the surface-modified fused silica is contacted with a slurry or dispersion of the molecular sieve and then heated at a temperature of 80° C. or greater, and often in the range of 80° to about 160° C. to effect an adhering film. The contact time does not appear to be critical. We have routinely used a contact time between about 50 and 60 minutes as a matter of convenience, although contact times as short is 2–3 minutes may suffice in appropriate circumstances.

The foregoing description is for a process where first the silica surface is treated with peroxide followed by contact with the sieve, but it needs to be emphasized that operationally the sequences may be combined by passing a slurry of the sieve in aqueous hydrogen peroxide through a fused silica capillary, followed by heating the resulting coated capillary. Which procedure is chosen is largely a matter of choice without significant effect on the outcome.

Although stable, well-adhering films may be realized with sieve particles whose size varies considerably, other considerations suggest that small sieve crystallites will permit better mass transfer, resulting in better separation and a higher number of theoretical plates per unit mass of sieve. Our preference is to use sieves with crystallites of about 2 microns average diameter or less, e.g., 0.1 to 2 microns, and excellent results have been obtained with crystallites in the size range of 0.1 to 1.0 microns, more particularly 0.2 to 0.8 microns.

Another method of obtaining a firmly adhering coating to a fused silica surface is to treat the fused silica with aluminum chlorhydrate (ACH) in the temperature range of about 50° C. to about 85° C. to form a strong, alumina-like film on the silica surface. ACH is a polymeric cationic hydroxyl inorganic aluminum complex formed by the hydrolysis of chloride-containing aluminum salts. It has been observed that this film has excellent adherence to fused silica as well as to molecular sieves and forms a strong intermediate layer between a molecular sieve deposited thereon and the silica surface. The mechanism of adhesion to fused silica is not well understood, but despite the lack of understanding there is a plethora of experimental observations demonstrating the physical stability of the film and its durability. Treatment with ACH is done generally at temperatures no greater than about 85° C. The modified fused silica surface is then contacted with a slurry of molecular sieve, which shows good adhesion to the film resulting from ACH treatment. As with the hydrogen peroxide variant, procedurally it is possible to combine the sequences by passing a slurry of the sieve and ACH through a fused silica capillary followed by heating the resulting coated, capillary generally at temperatures between about 80° and 160° C. although the temperature as a variable is not critical to the success of our invention.

Yet another variant utilizes a silica film deposited on the fused silica surface. When the film is deposited from a silica precursor, such as tetraethyl orthosilicate, which is subsequently hydrolyzed the resulting silica coating shows excellent adherence to fused silica and affords yet another inorganic layer intermediate to the fused silica surface and molecular sieve film. Subsequent deposition of molecular sieve from a slurry followed by heat fixation at temperatures in the interval 80° to about 160° C. affords a stable, strongly adherent thin film of molecular sieve. As with the foregoing methods it is possible to combine the sequences by passing a slurry of the silica precursor and sieve through a fused silica capillary followed by heating the resulting coated capillary in the temperature range indicated above. We also note that fixation can be combined with other heat treatments, e.g. removal of template, so that it is accurate to say that fixation can be conveniently achieved by heat treatment at temperatures of at least 80° C.

The use of an intermediate silica coating as described above is a specific variant, albeit a preferred one, of the more general deposition of a film of refractory inorganic oxide which adheres well to both the fused silica and molecular sieve, thereby serving as an inorganic binder in the resulting chromatographic column. One can, more generally, deposit an adherent coating of alumina, silica, magnesia, titania, boria, magnesia, chromia, vanadia, and any combinations thereof, on the fused silica surface via a suitable precursor of the refractory inorganic oxide. The precursor, such as tetraethyl orthosilicate in the case of silica, is one which is can be conveniently handled and passed through a fused silica column, with the resulting film subsequently converted to the oxide, generally by hydrolysis, to form a strongly adhering metal oxide coating on the fused silica surface. One reason silica is preferred is that it is chromatographically quite inert, i.e., its adsorbent capabilities to discriminate among organic species is extremely low. Thus, when used as a binder for molecular sieves the resulting separation characteristics are those of the sieve alone. In contrast, other refractory inorganic oxides are themselves selective adsorbents, thus their inherent properties are superimposed upon those of the molecular sieve and the result often is difficult to predict. Although we prefer an inert binder, with no separation capability associated therewith, one readily can envisage that use of non-inert or "active" binders might be advantageous in certain situations.

To complete our discussion, it needs to be mentioned that other pretreatments also will suffice. In particular, treatment of the fused silica surface with acid, base, and even steam appears to effect sufficient surface modification that subsequent formation of an adherent film of molecular sieve is readily attained. Although all these methods are simpler, at least in principal, that those discussed in greater detail above, the resulting films of molecular sieve tend to be somewhat less uniform in thickness or adherence than those resulting from the methods presented above. However, this is not to say that acid, base, or steam treatment is ineffective, or even defective, but rather that these treatments are less preferred than those described above.

Whatever the pretreatment method used to deposit the molecular sieve film, prior to use the coating is calcined, generally at temperatures of 400°–600° C., in order to drive off materials adsorbed by described above. the sieve. Where a templated sieve is used this also serves to remove template.

The fused silica capillaries which are generally used in gas liquid chromatography have an inside diameter in the range of 50 to 750 microns. The molecular sieve film thickness can vary considerably, depending upon the desired capacity, capillary inside diameter, degree of separation required, and so on, but may range from as little as about 0.5 microns up to as high as about 50 microns.

In an interesting variant the molecular sieve material itself is treated with hydrogen peroxide before it is deposited within the capillary. The effect of such treatment appears to be to increase the loading of the sieve, apparently by increasing the number of Si-OH/Al-OH groups on the sieve surface. Contact is effected under relatively mild conditions, e.g., 0.05–0.5 weight percent aqueous hydrogen peroxide at ambient temperature for several hours suffices.

The following merely exemplify our invention and do not limit it in any way.

EXAMPLES

Preparation of Chromatographic Column

Hydrogen Peroxide Pretreatment

The following description represents a typical preparation. All preparations were performed for columns approximately 40 meters in length with an inside diameter of 200–300 microns. An aqueous solution of hydrogen peroxide, 35 weight percent, was pumped through the column at a rate of 0.2 mL per minute at 80° C. until a total of 5 mL aqueous hydrogen peroxide was used. Water subsequently was pumped through the column to remove residual peroxide prior to pumping 5 mL of a silicalite slurry (1 weight percent silicalite) through the column at a rate of 0.1 mL per minute and at a temperature of 130° C. Excess material was blown out of the column by a stream of nitrogen and the coated column was heated to 150° C. both to evaporate residual water and to fix the silicalite onto the fused silica surface. This was followed by calcination at 500° C. for 2 hours in order to burn out the template present in the silicalite. When non-templated material was used (e.g., NaY, 13X) the material was heated at 450° C. in order to remove water and organics entrapped within the pores of the sieve.

If the same procedure was followed except that hydrogen peroxide was not used in the pretreating solution, no coating was formed. This demonstrates the necessity of using hydrogen peroxide in order to subsequently form an adherent coating of a molecular sieve.

Preparation of Chromatographic Column

ACH Pretreatment

A slurry of commercially available aluminum chlorohydrate (ACH) was diluted to no more than 2.5 weight percent ACH and a total of 5 mL was pumped through the column at a temperature under 85° C. The latter appears to be the maximum working temperature since oligomerization occurs at higher temperatures leading to an increase in viscosity with resulting column plugging. This was followed by pumping a slurry of molecular sieve (5 cc at 0.1 mL per minute) through the column, after which residual slurry was blown out of the column with a stream of nitrogen. The column then was heated at 150° C. to evaporate residual water and treated as described above.

Preparation of Chromatographic Column

TEOS Pretreatment

The capillary was filled with neat tetraethylorthosilicate at ambient temperature and permitted to remain in contact with the fused silica walls for approximately 30 minutes. The excess tetraethylorthosilicate was then purged from the column using nitrogen and the coating remaining on the walls was hydrolyzed by blowing a steam of moist air or nitrogen through the column. The nature of the gas is not particularly critical and the foregoing gases were convenient. Hydrolysis occurs readily at ambient temperature to give a coating of silica which is reactive toward molecular sieves (in the sense of providing an adherent surface). An aqueous slurry of the molecular sieve material is then passed through the column as described above, together with appropriate subsequent heat treatments.

Preparation of Chromatographic Column

Steam Pretreatment

Water was introduced into the column until it had filled approximately 3 feet of the capillary. The ends of the column were then sealed and the column was heated to 200° C. Following this treatment an aqueous slurry of the sieve is passed through the column as described above, together with appropriate subsequent heat treatments.

Chromatographic Separations

Columns of various sizes were prepared according to the foregoing methods using a film of silicalite (average particle diameter no more than 2 microns) as the stationary phase. The analyte for test purposes was ca. 1 cc of a mixture containing 100 ppm of each of the C1–C6 normal paraffins. Results are tabulated below for each of the four columns, A–D.

TABLE 1

Separations of Test Analyte

|  | A | B | C | D |
|---|---|---|---|---|
| Column length (meters)[b] | 10 | 40 | 50 | 50[c] |
| Pretreatment type | $H_2O_2$ | TESO | ACH | $H_2O_2$ |
| Carrier gas | air | $N_2$ | He | air |
| Flowrate (cc/mm) | 2 cc/min | 1 cc/min | 1 cc/min | 2 cc/min |
| Temp. program | 40°/2 min 20° C./min to 450° C. 450° C. 10 min | 35° C./5 min 5° C./min to 450° C. | 50° C./3 min 20° C./min to 450° C. | 75° C./2 min 20° C./min to 450° C. |
| Retention time (minutes) | | | | |
| C1 | 1.25 | 6.52[a] | 3.67[a] | 1.91 |
| C2 | 2.76 | 6.52[a] | 3.67[a] | 2.74 |
| C3 | 5.82 | 7.11 | 3.77 | 5.83 |
| C4 | 8.21 | 10.50 | 4.44 | 8.74 |
| C5 | 10.01 | 17.44 | 6.16 | 10.93 |
| C6 | 11.62 | 25.17 | 7.57 | 12.96 |

[a]Coelution of C1, C2.
[b]All columns were 300 microns inside diameter.
[c]Inside diameter of 200 microns

What is claimed is:

1. A gas chromatographic column, characterized by the absence of an organic component, for separation of materials present in a gas stream comprising: a fused silica capillary with an inside diameter from about 50 up to about 750 microns; a film of a refractory inorganic oxide on the inner surface of the capillary and strongly adhering thereto; a film of molecular sieve particles deposited on and adhering to said film of refractory inorganic oxide; and an unobstructed passage along the axis of said capillary; where said film of molecular sieve particles has a thickness from about 0.5 to about 50 microns and said particles have an average diameter from about 0.1 to about 2 microns.

2. A method of forming a film of molecular sieve particles on a fused silica surface comprising: modifying the silica surface by applying means selected from the group consisting of hydrogen peroxide activation, alumina deposition, and silica deposition to said surface to afford a modified silica surface; depositing a coating of molecular sieve particles of average size from about 0.1 to about 2 microns on the modified silica surface; fixing the deposited molecular sieve particles on the modified silica surface by heating at a temperature above about 80° C.; selectively removing molecular sieve particles not fixed to the modified silica surface; and recovering a film of molecular sieve particles fixed to the modified silica surface.

3. The method of claim 2 where hydrogen peroxide activation is effected by contacting the fused silica surface with an aqueous solution containing from about 3 to about 35 weight percent hydrogen peroxide at a temperature from about 60° to about 90° C.

4. The method of claim 3 where alumina deposition is effected by contacting the fused silica surface with an alumina precursor.

5. The method of claim 4 where the alumina precursor is an aqueous solution of aluminum chlorhydrate and said precursor is converted to alumina by hydrolysis.

6. The method of claim 3 where silica deposition is effected by contacting the fused silica surface with a silica precursor and converting said precursor to silica.

7. The method of claim 6 where the silica precursor is tetraethylorthosilicate and said precursor is converted to silica by hydrolysis of said tetraethylorthosilicate.

8. A process for the separation of at least two gaseous components in a mixture comprising flowing a gas stream containing at least two gaseous components through an interior unobstructed passage along the axis of a fused silica capillary having a modified interior surface and a film of molecular sieve particles affixed to the modified interior surface of said fused silica without the aid of an organic binder so as to effect differential absorption of at least two of said components.

9. The process of claim 8 where said film of molecular sieve particles is from about 0.5 up to about 50 microns thick.

10. The process of claim 8 where said molecular sieve particles has an average diameter from about 0.1 up to about 2 microns.

11. The process of claim 8 where the interior surface of the fused silica capillary is modified by means selected from the group consisting of hydrogen peroxide activation, alumina deposition, and silica deposition.

12. A process for determining by gas chromatography the presence of at least two of the components present in a mixture comprising: vaporizing said mixture prior to its introduction to a first terminus of a fused silica capillary whose interior surface has been modified by means selected from the group consisting of hydrogen peroxide activation, alumina deposition, and silica deposition; introducing the mixture into a first terminus of the fused silica capillary having an interior unobstructed passage along its axis and having on its modified interior surface a film from about 0.5 up to about 50 microns thick of molecular sieve particles of an average diameter from about 0.1 up to about 2 microns affixed to said fused silica, said molecular sieve manifesting differential absorption with respect to at least two of said components; flowing a gas stream along said unobstructed passage from said first terminus to a second terminus to separate said components along said passage; flowing at least a portion of said gas stream exiting the second terminus through a detector having a measurable response to at least two said components; and recording the response of said detector.

* * * * *